United States Patent [19]

Ogle et al.

[11] 4,444,066
[45] Apr. 24, 1984

[54] HIGH PRESSURE SAMPLE INJECTOR VALVE

[75] Inventors: David G. Ogle, Los Altos; John T. Taylor, Santa Clara, both of Calif.

[73] Assignee: Beckman Instruments, Inc., Fullerton, Calif.

[21] Appl. No.: 278,771

[22] Filed: Jun. 29, 1981

[51] Int. Cl.³ .............................................. G01N 1/10
[52] U.S. Cl. ............................. 73/863.72; 73/864.21; 73/864.84; 73/61.1 C
[58] Field of Search ........... 73/61.1 C, 863.71, 863.72, 73/863.73, 864.21, 864.84

[56] References Cited

U.S. PATENT DOCUMENTS

| | | | |
|---|---|---|---|
| 2,833,151 | 5/1958 | Harvey | 73/422 |
| 2,972,888 | 2/1961 | Lamkin | 73/863.72 |
| 2,973,117 | 2/1961 | Conklin | 222/3 |
| 3,203,249 | 8/1965 | Jentzsch et al. | 73/422 |
| 3,230,048 | 1/1966 | Skeggs | 23/253 |
| 3,297,053 | 1/1967 | McKinney | 73/863.72 |
| 3,504,799 | 4/1970 | Ogle et al. | 210/198 |
| 3,530,721 | 9/1970 | Hrdina | 73/864.21 |
| 3,533,295 | 10/1970 | Vesper | 73/422 |
| 3,559,458 | 2/1971 | Hrdina | 73/23.1 |
| 3,585,863 | 6/1971 | Hrdina | 73/422 |
| 3,862,038 | 1/1975 | Takeuchi et al. | 210/198 |
| 3,960,003 | 6/1976 | Beyer | 73/61.1 C |
| 4,068,528 | 1/1978 | Gundlefinger | 73/864.84 |
| 4,243,071 | 1/1981 | Shakelford | 137/625.46 |

Primary Examiner—S. Clement Swisher
Attorney, Agent, or Firm—R. J. Steinmeyer; F. L. Mehlhoff; W. H. May

[57] ABSTRACT

A high pressure valve for control of the injection of a sample into an analyzer system such as an amino acid analyzer with liquid column chromatography. The valve is designed in such a manner that no rinse solution that is used to cleanse the system after the injection of a particular sample will enter the liquid column. The valve operates in two positions and requires a minimum of movement between the two positions. In one position the valve allows for the injection of the sample into the liquid column. In the second position the valve allows for the entry of only a buffer solution into the liquid column and blocks the entry of any rinse solution that may flow through the system for cleansing after the injection of the sample. No residual rinse solution is allowed to remain within the valve prior to injection of either a sample or a buffer material into the liquid column.

6 Claims, 10 Drawing Figures

HIGH PRESSURE SAMPLE INJECTOR VALVE

BACKGROUND OF THE INVENTION

The present invention is directed to a high pressure sample injector valve and, more particularly, is directed to an injector valve that is used in an analyzer system such as in an amino acid analyzer which uses ion exchange liquid column chromatography.

In presently used systems such as in liquid chromatography it is extremely important that the sample which is being injected into the column not be mixed or diluted with any other type of material or liquid. It should only contact a buffer which will separate it from other samples and provide a border between various samples being injected into the system. However, it is also important that, after each sample is injected into the liquid column, the entire sample injection system be washed with some type of rinse solution in order that no impurities or sample carryover will be imparted into the next sample to be injected into the system and into the column.

However, the washing process, although eliminating the contamination which may occur by any residual portion of the previous sample being within the system, creates an additional problem with respect to the existence of some of the rinse solution remaining in the valve after the washing cycle. Consequently, when the next sample is injected through the valve, some of the rinse solution may be carried by the sample into the liquid column, causing a possible mixing and/or diluting of the sample and resulting in a degradation of the analysis to be accomplished in the liquid column chromatography.

Also, since the valving arrangement is for use in a high pressure system, some type of arcuate or rotative motion is imparted into the valving member to cause it to assume its proper position between either an inject or a bypass position. However, many of the presently used valves in such a system require a relatively large arcuate rotation of approximately sixty to ninety degrees. This rather large arcuate movement will cause significant wear on the sliding surfaces used in most valve construction due to the high loading forces that are necessary in the operation of a high pressure sample injector valve. Also, the need for a large arcuate movement in the valve will require rather complex and expensive linkages occupying significant space to accomplish the necessary movement.

SUMMARY OF THE INVENTION

The valve of the present invention is constructed in such a manner that no rinse solution is allowed to enter the liquid column. This is accomplished by having a passageway within the valve blocked from receiving any of the rinse solution. This particular passageway is in fluid communication with the liquid column during the bypass position of the valve to allow the flow of eluting buffer. When the valve is in the inject position for inserting the sample into the column, the eluting buffer passageway of the valve is in an isolated position and blocked from fluid communication with any of the valve ports of the valve. When the valve is moved back to the bypass position, only the buffer within the isolated passageway will enter the liquid column. Subsequent washing of the overall system after the injection of the fluid sample does not enter the isolated passageway of the valve. Therefore, no residual rinse solution is allowed to flow into the liquid column from any valve cavities or passages that may contain residues of the rinse solution.

The valve of the present invention is designed to operate in response to a relatively small arcuate movement of approximately thirty-six degrees (36°) and, therefore, limits the amount of wear to the mating surfaces of the valve. This small angle of motion permits direct use of a simple and low cost linear movement linkage to impart the necessary movement of the valve. Further, the valve of the present invention incorporates a means for providing a wash to the outer surfaces of the moving valve parts in order to reduce or prevent the buildup of salt crystals from the buffer that could scratch the valve parts or make valve actuation difficult.

The overall construction of the injector valve of the present invention provides a compact and uniform means for holding and for applying pressure on the sliding surfaces of the valve to provide balance and uniform contact between the surfaces. The invention incorporates an adjustable feature for providing the desired amount of pressure on the mating plates of the valve to ensure its proper operation.

DETAILED DESCRIPTION OF THE INVENTION

Figures 1, 2, 3:
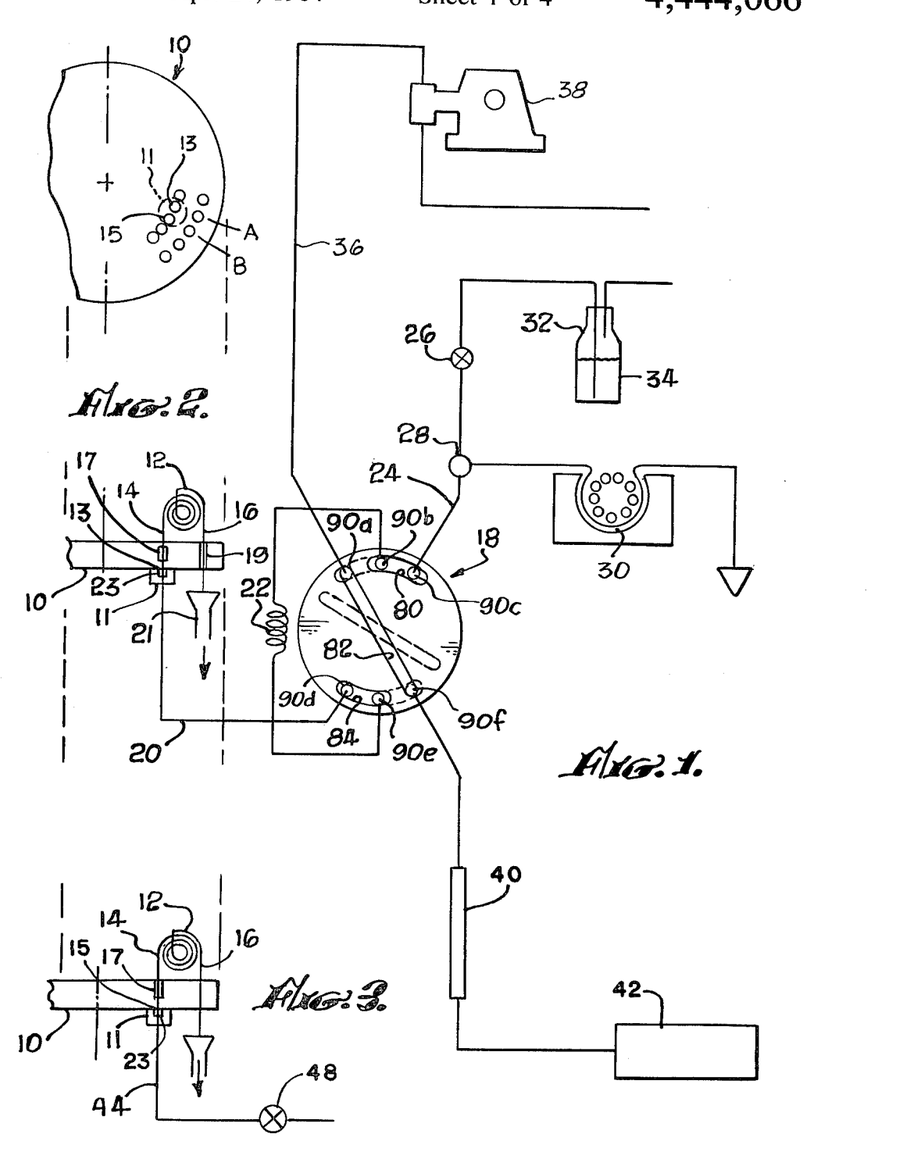
FIG. 1 is a schematic view of the overall amino acid analyzer system for use in liquid chromatography analysis, incorporating the valve of the present invention.
FIG. 2 is a partial schematic top view of the rotary table.
FIG. 3 is a partial schematic sectional view of the rotary table showing the coil dry position of the rotary table.

FIG. 1 is a schematic sketch of the complete sample injection system for an amino acid analyzer that automatically injects preloaded samples into a fluid stream at predetermined intervals for analysis by liquid column chromatography. A rotating sample table 10 is shown not only in FIG. 1, but also in FIGS. 2 and 3. The side view of the table in FIG. 1 shows the position for the transfer of the sample into the metering loop and subsequent rinse while the side view position in FIG. 3 shows the drying of the sample coil subsequent to injection of the sample. These operations will be described more fully below. The individual sample coil 12 contains a sample to be injected into the system at a predetermined time. With the use of the rotary table 10, a plurality of sample coils 12 can be positioned radially around the table, so that, as the table is indexed or advanced, each sample coil is moved into the sample transfer position A of the table shown in FIGS. 1 and 2. The sample coil 12 is essentially a spiral arrangement with two projecting ends.

Located below the movable table 10 is a stationary plate 11 having a transfer and rinse seal port 13 and a coil dry seal port 15. When the coil 12 is in the transfer and rinse position A on the table 10 as shown in FIGS. 1 and 2, the sealing end 14 of the coil is designed to engage a sealing junction 17 in the rotary table for sample transfer into the system. The other end 16 of the coil projects through an enlarged hole 19 for expelling overflow of waste into a waste funnel 21 during the rinse operation. Also, the rinse end 16 of the coil is the loading end of the coil for the initial loading of the sample into the coil prior to insertion into the rotary table. It should be noted that the sealing end 14 of the coil which is sealed into the seal junction 17 in the table is in alignment with the transfer and rinse port 13 of the stationary plate 11. O-rings 23 maintain the sealed engagement between the stationary plate 11 and the rotary table 10. The system sample supply line 20 is in engagement with the transfer and rinse port.

When the coil is in transfer position A, the sealing end 14 is connected to an injector valve 18 by the sample supply line 20. A more detailed description of the valve 18 will be explained below. The valve 18 is connected not only to a metering loop 22, but also to an exit line 24 which connects to a shut-off valve 26 via a T-connector 28 that is in communication with a transfer pump 30. Located in a reservoir 32 is a rinse solution 34. Also in communication with the valve 18 is a buffer source line 36 which is in fluid communication with a buffer pump 38 for supplying eluting buffer at high pressure (2000-5000 psig) through the valve 18. A liquid ion exchange column 40 is also in fluid communication with the high pressure valve 18. Connected in fluid communication with the liquid column 40 is a detection system 42.

When the sample coil 12 is moved to the coil dry position B on the rotary table as shown in FIGS. 2 and 3, the sealing end 14 of the coil is in alignment with the coil dry seal port 15 of the plate 11. A nitrogen flow line 44 is connected to the seal port 15 and a solenoid controlled valve 48 controls the flow of nitrogen into the sample coil 12 to dry the interior of the coil after the injection of the sample.

Figure 4:
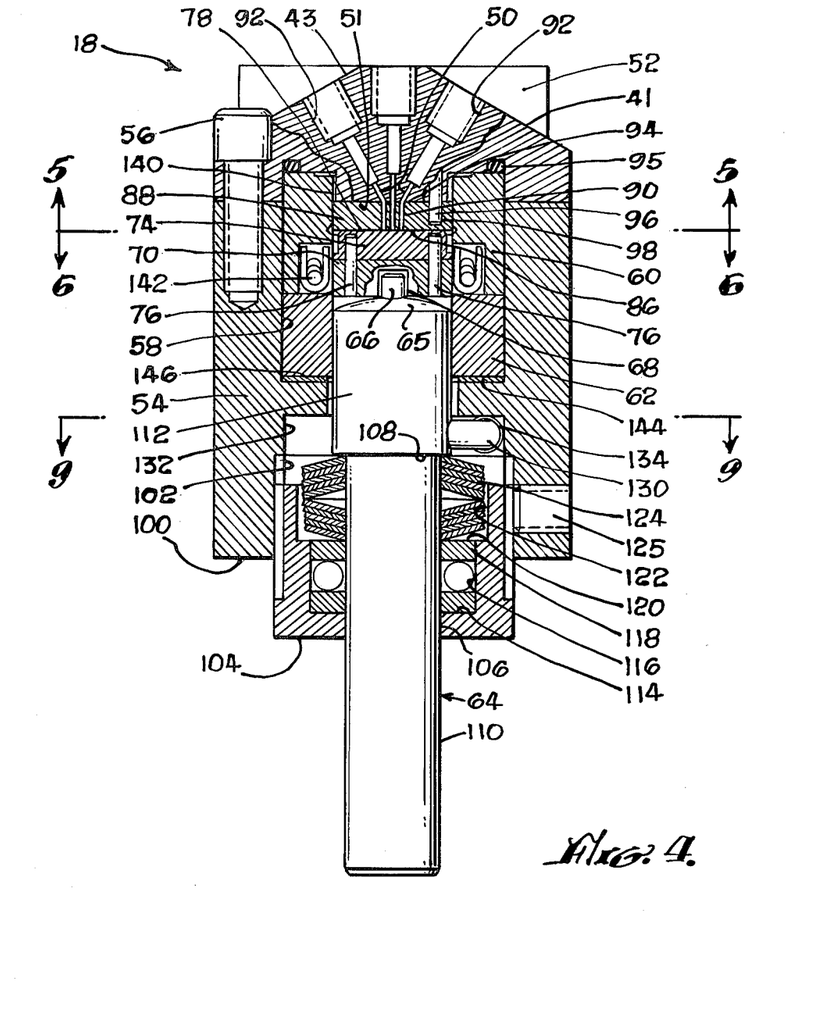
FIG. 4 is a sectional view of the valve of the present invention.
Figure 7:
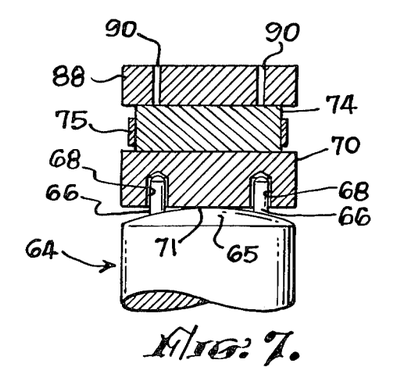
FIG. 7 is a partial sectional view showing the assembly of the moving valve parts.

Specific attention is now directed to FIG. 4 showing a partial sectional view of the valve 18 having a plurality of inlet ports 50 for fluid communication with the various portions of the amino acid analyzer described in FIG. 1. The valve 18 has a head 52 and a housing 54. The head 52 is secured to the housing 54 by a plurality of bolts or screws 56. Mounted within a generally cylindrical cavity 58 within the housing 54 is an upper bearing 60 and a lower bearing 62. These bearings are designed to properly align and secure the main moving parts of the sample injector valve 18. Positioned within the bearings 60 and 62 is a spindle 64 having at its upper end a spherical face 65 and two pins 66 which are received within apertures 68 in a rotor holder member 70. The interface of the pins 66 with aperture 68 in the holder member 70 allows torque to be transmitted from the spindle 64 to the rotor holder member 70. Reference is made to FIG. 7 which is a partial sectional view of the interface between the spindle 64 and the rotor holder member 70 at a 90° orientation with respect to the view in FIG. 2. The surface of the spherical face 65 contacts the flat lower surface 71 of the holder member 70 to provide a point of contact between the spindle and the holder member. This particular arrangement allows for a small degree of self-alignment of the holder member 70 with the rotor member 74 and the stationary or stator member 88. Also shown is a small metal containment ring 75 designed to add strength to the rotor 74 which is under very large compressive forces.

Interconnecting the rotor holder 70 and the rotor 74 in FIG. 4 are two alignment pins 76. Because movement of the spindle 64 will result in movement of the rotor holder 70, the alignment pins 76 will consequently cause the rotor 74 to move in concert with the rotor holder 70. On the upper surface 78 of the rotor 74 are a plurality of grooves 80, 82, and 84 shown more clearly in FIG. 6.

The upper surface 78 of the rotor 74 in FIG. 4 is in face-to-face contact with the mating surface 86 of a stationary or stator member 88 which has a plurality of ports or vertical channels 90. The ports 90 are shown more clearly in FIG. 5. The ends of the ports 90 adjacent the contact surface 86 of the stator member 88 are designed to be in contact with the various passageways 80, 82, and 84 of the rotor member 74 in FIG. 6. Similarly, in FIG. 4 the ports 90 are designed to be in fluid contact with the fitting ends 92 of the valve head 52. The fittings are used to connect fluid conduits in fluid communication with the respective ports 90 in the valve 18. It should be noted that the head 52 has two recessed flat surfaces 41 and 43 at the fitting end of the valve head which are inclined to increase the distance between the tube fittings 92 and allow for easier wrench across while at the same time allowing or permitting the ports 50 to be located closely adjacent each other.

Located at the interface between the fitting ends 92 and the ports 90 are O-rings 94 which provide a seal between the valve head 52 and the stator 88. The stator is restricted from turning in the valve head 52 by the dowel pin 96.

Figure 5:
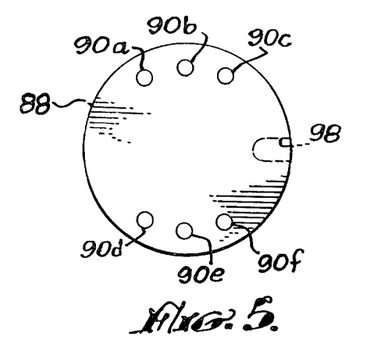
FIG. 5 is a view of the stator member of the valve taken along the line 5—5 in FIG. 4.
Figure 6:
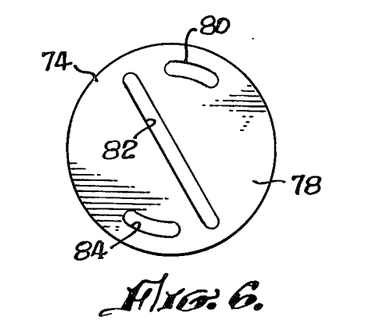
FIG. 6 is a view of the rotor member of the valve taken along the line 6—6 in FIG. 4.

Attention is directed to FIG. 5 showing in more detail the stationary member 88 while FIG. 6 discloses the rotor member 74. In a preferred embodiment of the present invention for use in an exemplary amino acid analyzer the stator 88 has an arrangement of six ports or channels 90a-90f. The stator 88 is generally cylindrical in shape and has an aperture 98 into which the holding pin or dowel pin 96 is positioned for holding the stator 88 stationary. This is shown more clearly in FIG. 4. The rotor member 74 in FIG. 6 has a pattern of three grooves 80, 82, and 84 on its top surface 78. When the rotor member 74 and the stator member 88 are aligned and assembled as shown in FIG. 4, the various ports 90a-90f are designed to align with the extremities of the pattern of passageways or grooves 80, 82, and 84 of the rotor 74. This will be explained in more detail below.

With reference to FIG. 4, located near the lower end 100 of the housing 54 is an interior cavity 102 which is designed to threadably receive a loading screw 104. The loading screw has an aperture 106 which is designed to allow receipt of the spindle 64. It should be noted that the spindle 64 has a shoulder portion 108 representing the difference in diameter between the lower portion 110 of the spindle and the larger upper portion 112 of the spindle. Located in the interior of the loading screw 104 is a first shoulder 114 representing the difference in the diameter between the aperture 106 and the interior cavity 116 which is designed to receive the bearing 118. Also, a second shoulder 120 is located within the loading screw which is designed to establish an enlarged cavity area 122 for receipt of spring washers 124 which preferably could be belleville type washers. It should be noted that these belleville type washers 124 will reside between the shoulder 108 of the spindle 64 and the shoulder 120 on the loading screw 104. As the loading screw is threaded into the lower end 100 of the housing 54, the washers 124 will be compressed and will create a pressure on the spindle 64 toward the rotor holder 70 to force the rotor 74 into tight face-to-face relation with the stator 88. The head 52 being connected to the housing 54 provides a bearing surface 51 against which the stator is forced as the loading screw is tightened. The loading screw permits adjustment in the pressure between the stator and the rotor in order to provide the requisite interface contact for proper operation of the valve.

A set screw 125 is located in the housing 100 and is designed to contact the locking screw 104 to securely hold it in its correct location once the proper amount of compression has been imparted by the belleville washers 124 against the spindle 64 and rotor 74. The tip of the locking screw 104 is preferably nylon to prevent damage to the threads of the loading screw.

Figure 9:
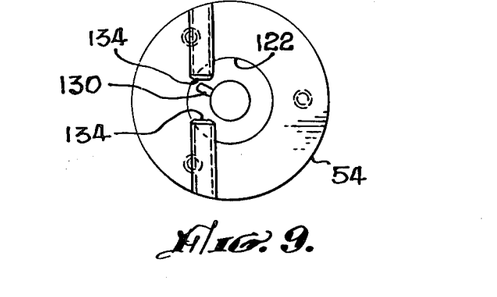
FIG. 9 is a view of the stop limits for the arcuate movement of the valve spindle taken along the line 9—9 in FIG. 4.

In order to control the rotative arcuate motion of the spindle 64, a stop pin 130 in FIG. 4 extends radially outward from the upper portion 112 of the spindle into an annular cavity 132 above the loading screw 104. The stop pin 130 operates in conjunction with a pair of opposing adjustable contact stops 134. Reference is made to FIG. 9 showing the contact stops 134 which are designed to limit the arcuate motion of the spindle 64 as a result of the projecting contact pin 130 contacting the stops 134. These stops are threaded into housing 54 to provide adjustability in the amount of arc through which the spindle can rotate.

With respect to FIG. 4, a cavity 140 adjacent the stator 88 is designed to receive a solvent such as water through a port (not shown) and direct the water to the cylindrical faces of the stator 88 and the rotor 74 to prevent the possible buildup of any salt from samples or buffer that could make the valve actuation difficult. A port (not shown) is also utilized to provide an exit for the water rinse. A spring loaded seal 142 in conjunction with the O-ring 95 is designed to prevent any leakage from the cavity area 140 to either the valve actuating mechanism and to the outside of the valve.

It should be noted that a spring washer 144 is mounted between the shoulder 146 of the housing 54 and the bearing 62. The spring washer 144 will provide added pressure on the bearing 62 and against the bearing 60 and the O-ring seal 95.

Figure 10:
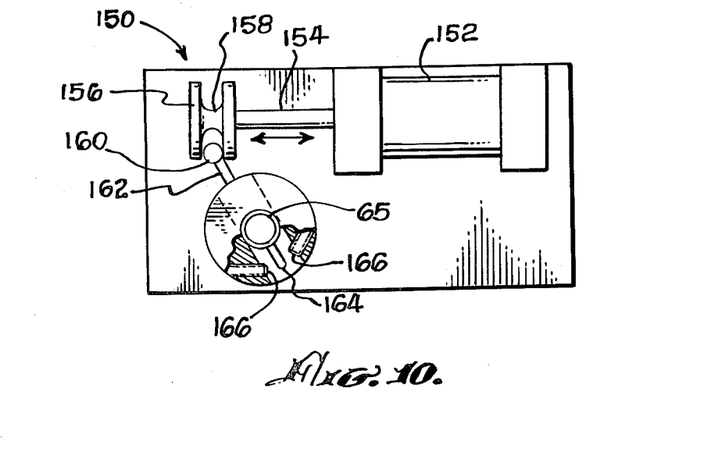
FIG. 10 is a top view of the actuator mechanism to operate the valve.

A rotary actuator mechanism 150 is shown in FIG. 10 having a pneumatic cylinder 152 with a piston rod 154 and a cylindrical yoke 156. Movement of the piston rod 154 along its longitudinal axis is controlled by the actuation of the pneumatic or hydraulic cylinder 152. The cylindrical yoke 156 has an annular groove 158. Mounted within the annular groove 158 is a ball joint 160 that is connected to a lever 162. With reference to FIG. 4, the lower end of the spindle 64 has an extension spindle 65 to which the lever 162 is connected as shown in FIG. 10. With reference to FIG. 10, the extension spindle 65 is shown having the projecting stop pin 164 that contacts the two contact points 166. Therefore, any actuation of the piston rod 154 along its longitudinal axis will cause the lever 162 to impart an arcuate movement of the extension spindle 65 and the spindle 64. This will result, as shown in FIG. 4, in the relative movement of the rotor 74 with respect to the stator 88. Both the contact stops 134 of FIGS. 4 and 9 as well as the stops 166 in FIG. 10 which control the throw of the piston rod 154 are adjustable so that accommodation is possible to retain valve parts in proper alignment and operation as the wear and possible loosening of the parts occurs.

Figure 8:
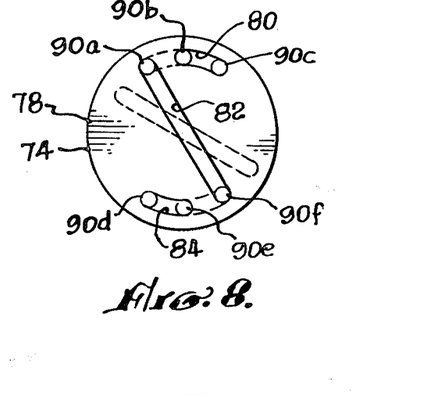
FIG. 8 is an enlarged view of the passageways within the rotor member and showing the alternate positions of the valve.

In order to more specifically describe the movement of the high pressure injector valve, attention is directed to FIG. 8, showing the rotor 74 with its top surface 78 having a plurality of passageways 80, 82, and 84. The position of the passageways in solid lines shows their orientation when the valve is in the bypass position. The orientation of the passageways shown in phantom is the position they assume when the valve has been rotated to the inject position. The relative positions of the ports 90a–90f of the stator member are represented by the various circular locations at the extremities of the passageways when the valve is in the bypass position. The plurality of ports 90a–90f remain stationary, since the passageways 80, 82, and 84 are rotated. Consequently, when the rotor 74 is rotated to the inject position, the passageway 80 moves to the left with respect to FIG. 8, so that its extremities are in fluid communication with ports 90a and 90b. Central passageway 82 is rotated in a counterclockwise direction with respect to FIG. 8 so that its extremities are no longer in fluid communication with any of the ports 90a–90f. Further, passageway 84 is shifted to the right with respect to FIG. 6 so that its extremities are in fluid communication with ports 90e and 90f.

The overall amino acid analyzer system to which the various ports 90a–90f of the high pressure valve 18 are connected is shown more clearly in FIG. 1. Similarly, the valve 18 shown in FIG. 1 represents the passageways 80, 82, and 84 in solid line when the valve is in the bypass position and are shown in phantom when it is in the inject position. Therefore, when the valve 18 is in the bypass position, the central passageway 82 is in contact at its extremities with port 90a and port 90f so that there is a flow of the buffer from the buffer source line 36 through port 90a, passage 82, port 90f and into the column 40. Similarly, when the valve 18 is in the bypass position, the passageway 80 is connected to the metering loop 22 and the rinse solution line 24. Also, the passageway 84 is in contact with ports 90d and 90e for contact with the sample supply line 20 and the metering loop 22. In the bypass position, a sample is drawn by a vacuum created by the transfer pump 30 into the sample supply line 20 through port 90d, passage 84, port 90e and into the metering loop 22. The sample is drawn completely into the metering loop 22 and slightly past the port 90c to ensure complete filling of the metering loop 22.

After all of the sample is inserted into the metering loop, the valve 18 is actuated by the actuating system shown in FIG. 10 to rotate the rotor member 74 to the inject position with the passageways shown in phantom in FIG. 1. In this position, the central passageway 82 which contains a buffer will be isolated or blocked from connection with any of the ports 90a–90f. The passageway 80 is now in communication with the ports 90a and 90b. Also, the passageway 84 is in contact with ports 90e and 90f. The sample in the metering loop 22 is then pumped at very high pressure of as much as 5000 psig by the use of the buffer from the source line 36 and high pressure pump 38 through the port 90a, the passageway 80, the port 90b and into the metering loop 22 to force the sample out through the port 90e, passageway 84, and port 90f into the column 40.

Once the sample has been completely placed into the column 40, after a time delay, the actuator shown in FIG. 10 moves the valve 18 back to its bypass position with the passageways oriented as shown in solid lines. At this point, in order to cleanse the system before the next sample is placed into it, a rinse solution 34 from the source reservoir 32 is forced through the line 24 into port 90c, through passageway 80, port 90b and into the metering loop 22. The rinse solution continues through port 90e, passageway 84, and port 90d. The rinse continues through the sample line 20 and out through the sample coil 12 to a waste collector 21. The sample table 10 will next be indexed to move the sample coil 12 to the drying position B for connection to line 44. Nitrogen is introduced through control valve 48 through the sample coil 12 to dry it.

When the valve has been returned to its bypass position, the buffer which is located in the central passageway 82 again flows with the buffer from the buffer source line 36 into the column 40. No rinse solution enters the central passageway 82 and, therefore, none of the wash solution is allowed to enter the column 40. This is very important so that it will not dilute, mix with the sample, or add an artifact to the chromatogram which is in the liquid column 40 for analysis by liquid column chromatography which operates with a visible wavelength detection system 42 to determine the amino acid composition. Periodically, water may be introduced into the cavity 140 of FIG. 4 to flush any salt crystals of the buffer or sample material which may have collected and solidified at the outside or circumferential interface of the rotor and stator.

The entire cycle is then repeated with the insertion of a new sample from a subsequent sample coil. The sample coils 12 in FIG. 1 are generally placed on a circular table 10 so that numerous samples are sequentially inserted into the column 40. The system is an automatic sequence using a microprocessor based programmer to control the various elements in the system for the injection of the sample, movement of the valve, rinsing the system, etc.

It is important to note that the actuation of the rotor 74 of the valve shown more specifically in FIG. 8 requires movement of the rotor 74 of only approximately 36°. Hence, less wear occurs on the sliding surfaces of the rotor and stator. This allows for the use of a simple and compact actuator system as shown in FIG. 10 to activate and move the valve 18.

The rotor 74 is preferably made of a material with properties that provide for a high pressure seal and low friction when in contact with the stator 88. Such a material may be a graphite filled polymeric (resilient) material. The bearings 60 and 62 are preferably made of a fluorocarbon material. The valve head 52 is preferably made from a high grade stainless steel alloy while the body or housing 54 can be made of a lesser cost, easier-to-machine alloy (such as aluminum), since it will not be in contact with any corrosive solvents.

The stator member 88 is preferably made of a high compressive strength material capable of being lapped to a very flat and smooth finish with suitable corrosion resistance such as an aluminum oxide material. The materials of construction used in the present invention allow for the use of this valve with most any aqueous buffer or solvent mobile phase as opposed to systems that are presently used. In many instances it is necessary with existing systems to preclude the use of halide ion buffers. The valve of the present invention utilizes a high nickel and chromium stainless steel alloy (Carpenter 20C$_b$-3) for the head 52 as well as an aluminum oxide (ceramic) for the stator member 88 and a graphite-fiber filled polyphenylene sulfide material for the rotor member.

It may be possible to replace the plurality of O-rings 94 that are adjacent the ports 90 between the head 52 and the stator 88 by the use of a sealing plate made of a polymeric (plastic) material. This plate could establish a seal between the head 52 and the stator 88 due to the actual loading of the assembly caused by the loading screw 104.

What is claimed is:

1. A sample injector valve for use in an analyzer system having a sample source, a buffer source, a measuring loop, an analyzer column, and a rinse solution source, said injector valve comprising:
   a housing;
   a stator member mounted in said housing and having a plurality of ports, said ports being in fluid communication respectively with said sample source, said buffer source, said measuring loop, said analyzer column and said rinse solution source;
   a rotor member mounted in said housing in juxtaposed relation with said stator member and having a generally flat contact surface in contact with a generally flat surface of said stator member, said rotor member movable between a bypass and an inject position, said movement between said bypass and inject positions being less than 60°, said rotor having a plurality of passageways, one of said passageways being in fluid communication with said buffer source and said analyzer column when said rotor member is in said bypass position, said one of said passageways not being in fluid communication with any of said ports when said rotor member is in said inject position, said one passageway only receiving buffer material for introduction to said analyzer column when said rotor member is in said bypass position;
   bearing means in said housing surrounding said rotor for maintaining alignment between said stator member and said rotor member;
   a bearing surface adjacent one end of said housing;
   a biasing spring mounted in said housing for applying a force toward said bearing surface, said rotor and said stator being located between said biasing spring and said bearing surface;
   adjusting means external to said valve for adjusting the force of said biasing spring on said rotor and said stator toward said bearing surface.

2. A sample injector valve for use in an analyzer system having a sample source, a buffer source, a measuring loop, an analyzer column, and a rinse solution source, said injector valve comprising:
   a housing;
   a stator member mounted in said housing and having a plurality of ports, said ports being in fluid communication respectively with said sample source, said buffer source, said measuring loop, said analyzer column and said rinse solution source;
   a motor member mounted in said housing in juxtaposed relation with said stator member and having a generally flat contact surface in contact with a generally flat surface of said stator member, said rotor member movable between a bypass and an inject position, said movement between said bypass and inject positions being less than 60°, said rotor having a plurality of passageways, one of said passageways being in fluid communication with said buffer source and said analyzer column when said rotor member is in said bypass position, said one of said passageways not being in fluid communication with any of said ports when said rotor member is in said inject position, said one passageway only receiving buffer material for introduction to said analyzer column when said rotor member is in said bypass position;

bearing means in said housing surrounding said rotor for maintaining alignment between said stator member and said rotor member;

a bearing surface adjacent one end of said housing;

a biasing spring mounted in said housing for applying a force toward said bearing surface, said rotor and said stator being located between said biasing spring and said bearing surface;

adjusting means external to said valve for adjusting the force of said biasing spring on said rotor and said stator toward said bearing surface, said adjusting means comprising a loading screw threaded into said housing, said loading screw compressing said biasing spring to exert more force on said rotor and said stator as said loading screw is moved toward said bearing surface.

3. A sample injector valve for use in an analyzer system having a sample source, a buffer source, a measuring loop, an analyzer column, and a rinse solution source, said injector valve comprising:

a housing;

a stator member mounted in said housing and having a plurality of ports, said ports being in fluid communication respectively with said sample source, said buffer source, said measuring loop, said analyzer column and said rinse solution source;

a rotor member mounted in said housing in juxtaposed relation with said stator member and having a contact surface in contact with a surface of said stator member, said rotor member movable between a bypass and an inject position, said rotor having a plurality of passageways, one of said passageways being in fluid communication with said buffer source and said analyzer column when said rotor member is in said bypass position, said one of said passageways not being in fluid communication with any of said ports when said rotor member is in said inject position, said one passageway only receiving buffer material for introduction to said analyzer column when said rotor member is in said bypass position;

means for holding said stator member and said rotor member firmly within said housing;

a spindle interconnected with said rotor in such a manner that rotative movement of said spindle will impart a corresponding rotative movement in said rotor;

a lever connected to said spindle;

a piston rod;

means for imparting linear motion to said piston rod;

an annular groove on said piston rod; and a ball joint on said lever, said ball joint riding in said annular groove.

4. A system analyzer comprising:

a rotary valve having a stator member and a rotor member in face-to-face relation with each other, said rotor member having at least one passageway, said stator member having a plurality of ports, said rotor member movable between a first position and a second position;

a sample source in fluid communication with a first port of said plurality of ports, a measuring loop in fluid communication with second and third ports of said plurality of ports;

a buffer source in fluid communication with a fourth port of said plurality of ports;

an analyzer column in fluid communication with a fifth port of said plurality of ports; and a rinse solution source in fluid communication with a sixth port of said plurality of ports, said passageway establishing fluid communication between said buffer source and said analyzer column when said rotor member is in said first position, said plurality of ports being arranged in such a manner that one of said rinse and said sample sources is in fluid communication with said measuring loop when said rotor is in said first position, said passageway being blocked from fluid communication with any of said ports when said rotor is in said second position, said sample source being in fluid communication with said analyzer column when said rotor is in said second position, said passageway containing only buffer when in said first and second positions so that no rinse will enter said analyzer column.

5. A sample injector valve for use in an analyzer system having a sample source, a buffer source, a measuring loop, an analyzer column, and a rinse solution source, said injector valve comprising:

a housing;

a stator member mounted in said housing and having a plurality of ports, said ports being in fluid communication respectively with said sample source, said buffer source, said measuring loop, said analyzer column and said rinse solution source;

a rotor member mounted in said housing in juxtaposed relation with said stator member and having a generally flat contact surface in contact with a generally flat surface of said stator member, said rotor member movable between a bypass and an inject position, said movement between said bypass and inject positions being less than 60°, said rotor having a plurality of passageways, one of said passageways being in fluid communication with said buffer source and said analyzer column when said rotor member is in said bypass position, said one of said passageways not being in fluid communication with any of said ports when said rotor member is in said inject position, said one passageway only receiving buffer material for introduction to said analyzer column when said rotor member is in said bypass position, means for holding said stator member and said rotor member firmly within said housing;

means for rotating said rotor member between said bypass and injector positions;

said rotor member being cylindrical; and wherein said valve additionally comprises a solvent source in fluid communication with said rotor member to rinse said rotor member to ensure proper movement of said rotor member.

6. A sample injector valve for use in an analyzer system having a sample source, a buffer source, a measuring loop, an analyzer column, and a rinse solution source, said injector valve comprising:

a housing;

a stator member mounted in said housing and having a plurality of ports, said ports being in fluid communication respectively with said sample source, said buffer source, said measuring loop, said analyzer column and said rinse solution source;

a motor member mounted in said housing in juxtaposed relation with said stator member and having a generally flat contact surface in contact with a generally flat surface of said stator member, said rotor member movable between a bypass and an inject position, said movement between said bypass and inject positions being less than 60°, said rotor having a plurality of passageways, one of said passageways being in fluid communication with said buffer source and said analyzer column when said rotor member is in said bypass position, said one of said passageways not being in fluid communication with any of said ports when said rotor member is in said inject position, said one passageway only receiving buffer material for introduction to said analyzer column when said rotor member is in said bypass position, means for holding said stator member and said rotor member firmly within said housing;

means for rotating said rotor member between said bypass and injector positions;

said rotor member being cylindrical;

said valve including a solvent source in fluid communication with said rotor member to rinse said rotor member to ensure proper movement of said rotor member; and a cavity adjacent said rotor member to receive and direct said solvent to said rotor member.

* * * * *